United States Patent [19]
Daniels et al.

[11] 4,284,764
[45] Aug. 18, 1981

[54] PROCESS FOR THE PREPARATION OF 5-FLUORO-5-DEOXY AND 5-EPI-FLUORO-5-DEOXY-4,6-DI-O-(AMINO-GLYCOSYL)-1,3-DIAMINOCYCLITOLS AND NOVEL 5-FLUORO-5-DEOXY AND 5-EPI-FLUORO-5-DEOXY DERIVATIVES PRODUCED THEREBY

[75] Inventors: Peter J. L. Daniels, Cedar Grove; Dinanath Rane, Verona, both of N.J.

[73] Assignee: Schering Corporation, Kenilworth, N.J.

[21] Appl. No.: 122,097

[22] Filed: Feb. 19, 1980

Related U.S. Application Data

[63] Continuation-in-part of Ser. No. 893,638, Apr. 4, 1978, abandoned, which is a continuation-in-part of Ser. No. 792,825, May 2, 1977, abandoned.

[51] Int. Cl.$^3$ ...................... A61K 31/71; C07H 15/22

[52] U.S. Cl. .................................. 536/10; 424/180; 536/17 R

[58] Field of Search .............................. 536/17 R, 10

[56] References Cited

U.S. PATENT DOCUMENTS

| 3,972,930 | 8/1976 | Daum et al. | 536/17 R |
| 4,000,262 | 12/1976 | Daniels | 536/17 R |
| 4,029,883 | 6/1977 | Hiraga et al. | 536/17 R |
| 4,065,616 | 12/1977 | Umezawa et al. | 536/17 R |

Primary Examiner—Johnnie R. Brown
Attorney, Agent, or Firm—Elizabeth A. Bellamy; Anita W. Magatti; Mary S. King

[57] ABSTRACT

A novel process whereby 4,6-di-O-(aminoglycosyl)-1,3-diaminocyclitols are reacted with a dialkylaminosulfur trifluoride to produce novel 5-fluoro-5-deoxy and 5-epi-fluoro-5-deoxy-4,6-di-O-(aminoglycosyl)-1,3-diaminocyclitol antibacterial agents.

10 Claims, No Drawings

PROCESS FOR THE PREPARATION OF 5-FLUORO-5-DEOXY AND 5-EPI-FLUORO-5-DEOXY-4,6-DI-O-(AMINOGLYCOSYL)-1,3-DIAMINOCYCLITOLS AND NOVEL 5-FLUORO-5-DEOXY AND 5-EPI-FLUORO-5-DEOXY DERIVATIVES PRODUCED THEREBY

CROSS-REFERENCE TO RELATED APPLICATIONS

This application is a continuation-in-part of co-pending application Ser. No. 893,638 filed Apr. 4, 1978, now abandoned, which is a continuation-in-part of application Ser. No. 792,825 filed May 2, 1977, now abandoned.

FIELD OF THE INVENTION

This invention relates to a novel process and to novel compositions-of-matter produced thereby.

Specifically, this invention relates to a process for preparing 5-fluoro-5-deoxy and 5-epi-fluoro-5-deoxy derivatives of 4,6-di-O-(aminoglycosyl)-1,3-diaminocyclitols.

Particularly, this invention relates to a process for preparing 5-fluoro-5-deoxy and 5-epi-fluoro-5-deoxy derivatives of 4,6-di-O-(aminoglycosyl)-1,3-diaminocyclitol antibiotics including gentamicins, sisomicin, verdamicin, tobramycin, Antibiotic G-418, Antibiotic 66-40B, Antibiotic 66-40D, Antibiotic JI-20A, Antibiotic JI-20B, Antibiotic G-52, Antibiotic Mu-1, Antibiotic Mu-4, kanamycin A, kanamycin B, 3',4'-dideoxykanamycin B and their 1-N-acyl and 1-N-alkyl derivatives.

Still further, this invention relates to novel 5-fluoro-5-deoxy and 5-epi-fluoro-5-deoxy-4,6-di-O-(aminoglycosyl)-1,3-diaminocyclitols produced by the process of our invention, and their pharmaceutically acceptable acid addition salts, which compounds exhibit antibacterial activity.

PRIOR ART

U.S. Pat. No. 3,972,930 issued Aug. 3, 1976 to Daum et al, describes a microbiological process for the preparation of 5-fluoro-5-deoxy gentamicins $C_1$, $C_{1a}$ and $C_2$. Said microbiological process is accomplished by subjecting the aminocyclitol, 5-fluoro-2,5-dideoxystreptamine to the action of a microorganism identified as *Micromonospora purpurea* ATCC 31,119 (a mutant of *Micromonospora purpurea* NRRL 2953). In addition, there is disclosed the conversion of the foregoing 5-fluoro-5-deoxy gentamicins to their 1-N-(S)-(ν-amino-α-hydroxybutyryl) derivatives (hereinafter identified as 1-N-(S)-HABA derivatives) via chemical transformation.

By our invention, we have developed a novel chemical process whereby a 4,6-di-O-(aminoglycosyl)-1,3-diaminocyclitol having a 5-epi-hydroxyl or a 5-hydroxyl group, upon reaction with a dialkylaminosulfur trifluoride, is stereospecifically and solely converted to the corresponding 5-fluoro-5-deoxy or 5-epi-fluoro-5-deoxy derivative. Therefore, by our invention, there are produced novel 5-fluoro-5-deoxy and 5-epi-fluoro-5-deoxy-4,6-di-O-(aminoglycosyl)-1,3-diaminocyclitols which cannot be made by the microbiological process of Daum et al.

GENERAL DESCRIPTION OF THE INVENTION PROCESS ASPECT

The process aspect of this invention resides in the concept of preparing and isolating the 5-fluoro-5-deoxy and 5-epi-fluoro-5-deoxy derivatives of 4,6-di-O-(aminoglycosyl)-1,3-diaminocyclitols or their 1-N-X derivatives wherein X is —CH₂Y or

wherein Y is a member selected from the group consisting of hydrogen, alkyl, alkenyl, cycloalkyl, cycloalkylalkyl, hydroxyalkyl, aminoalkyl, alkylaminoalkyl, aminohydroxyalkyl and alkylaminohydroxyalkyl, said Y having up to 4 carbon atoms, and when substituted by both amino and hydroxyl groups, said groups are on different carbon atoms.

We have found by our invention, a novel stereospecific chemical process to prepare solely a 5-fluoro-5-deoxy or a 5-epiifluoro-5-deoxy-aminoglycoside from a corresponding aminoglycoside having a free 5-epi-hydroxyl or 5-hydroxyl group. Thus, suitable starting aminoglycosides of our process include 4,6-di-O-(aminoglycosyl)-1,3-diaminocyclitols selected from the group consisting of gentamicin A, gentamicin B, gentamicin $B_1$, gentamicin $C_1$, gentamicin $C_{1a}$, gentamicin $C_2$, gentamicin $C_{2a}$, gentamicin $C_{2b}$, gentamicin $X_2$, sisomicin, verdamicin, tobramycin, Antibiotic G-418, Antibiotic 66-40B, Antibiotic 66-40D, Antibiotic JI-20A, Antibiotic JI-20B, Antibiotic G-52, Antibiotic Mu-1, Antibiotic Mu-4, kanamycin A, kanamycin B and 3',4'-dideoxykanamycin B, and their 5-epi analogs, or the 1-N-X derivatives of the foregoing.

The introduction of the 5-fluoro-5-deoxy or 5-epi-fluoro-5-deoxy moiety on an aminoglycoside via displacement of a 5-O-mesylate group has been unsuccessful with previously known fluorinating agents such as NaF, LiF and KF. We have now found that the introduction of such a moiety is possible with the fluorinating agents of our process, i.e. dialkylaminosulfur trifluorides on a 5-epi-hydroxyl or 5-hydroxyl group.

Our process comprises the reaction of a dialkylaminosulfur trifluoride with a 4,6-di-O-(aminoglycosyl)-1,3-diaminocyclitol or its 1-N-X derivative, having all its amino and hydroxyl functions, other than the 5-epi-hydroxyl or 5-hydroxyl function, protected, in an inert organic solvent in the temperature range of from about −100° C. to about −50° C. Thereupon, the so-formed 5-fluoro-5-deoxy or 5-epi-fluoro-5-deoxy-N-protected-O-protected-4,6-di-O-(aminoglycosyl)-1,3-diaminocyclitol or its 1-N-X derivative, is deprotected and isolated to obtain the requisite 5-fluoro-5-deoxy or 5-epi-fluoro-5-deoxy-4,6-di-O-(aminoglycosyl)-1,3-diaminocyclitol or its 1-N-X derivative.

In our process, it is first necessary to "suitably protect" the amino and hydroxyl functions on the aminoglycoside, other than the hydroxyl function in the 5-position. By "suitably protect" we mean introducing those groups utilized to protect amino and hydroxyl functions during chemical reactions. The choice of the proper protecting group is within the ordinary ability of one skilled in the art and depends on various factors including whether an amino or hydroxyl group is being protected, subsequent reaction conditions, and conditions desired for removal. Preferred amino protecting groups of this invention are benzyloxycarbonyl, methoxycarbonyl, ethoxycarbonyl,2,2,2-trichloroethoxycarbonyl and benzoyl; our preferred hydroxyl protecting groups are acetyl and benzoyl. The methodology for preparing such N-protected-O-protected-4,6-di-O-(aminoglycosyl)-1,3-diaminocyclitols having a free 5-hydroxyl group is described in U.S. Pat. No. 4,000,261. Additionally, this patent teaches the preparation of 5-epi-4,6-di-O-(aminoglycosyl)-1,3-diaminocyclitols, which, in turn, using the same methodology, can be protected leaving the 5-epi-hydroxyl group free. We have found that those 4,6-di-O-(aminoglycosyl)-1,3-diaminocyclitols wherein the 6-O-aminoglycosyl does not contain a tertiary hydroxyl group at the 4"-position, e.g. gentamicin A, Antibiotics 66-40B, 66-40D, tobramycin, kanamycin A, kanamycin B and 3',4'-dideoxykanamycin B and their 5-epi analogs are more readily protected via methods as described hereinafter for tobramycin in the Preparations and Examples.

The preferred dialkylaminosulfur trifluorides of our invention are diethylaminosulfur trifluoride, dimethylaminosulfur trifluoride, and pyrrolidinosulfur trifluoride, with diethylaminosulfur trifluoride, hereinafter called DAST, being the most preferred. The dialkylaminosulfur trifluorides are known and described by Middleton in J. Org. Chem., Vol. 40, No. 5, 1975 (pp. 574–578).

The reaction is usually carried out in an atmosphere of argon, although this is not a requisite, and in an inert organic solvent. We prefer the use of methylene chloride, however, other solvents such as diglyme, chloroform, carbon tetrachloride and trichlorofluoromethane can be used. The temperature utilized in our process can be in the range of from about −100° C. to about −50° C. but is best carried out at about −80° C. to about −60° C.

Thusly, in our process an N-protected-O-protected-4,6-di-O-(aminoglycosyl)-1,3-diaminocyclitol having a free 5-epi-hydroxyl or 5-hydroxyl group is usually reacted with at least 5 equivalents of a dialkylaminosulfur trifluoride, preferably DAST, in an inert organic solvent in the temperature range of from about −100° C. to about −50° C. for about 2 hours, then allowed to warm to room temperature and treated with sodium bicarbonate. The organic phase is then separated out, washed, dried, and evaporated to a residue comprising the 5-fluoro-5-deoxy or 5-epi-fluoro-5-deoxy-N-protected-O-protected-4,6-di-O-(aminoglycosyl)-1,3-diaminocyclitol. Utilizing deprotecting and purification techniques well known in the art, the 5-fluoro-5-deoxy or 5-epi-fluoro-5-deoxy-4,6-di-O-(aminoglycosyl)-1,3-diaminocyclitols of our invention are obtained.

The 1-N-X derivatives of our 5-fluoro-5-deoxy or 5-epi-fluoro-5-deoxy-aminoglycosides may be obtained via various methods. For example, the 1-N-X derivative may be introduced onto the parent aminoglycoside prior to N,O-protection and fluorination; alternatively the 1-N-X derivative may be introduced subsequent to the preparation of the 5-fluoro-5-deoxy-or 5-epi-fluoro-5-deoxyaminoglycoside. Procedures for introducing the 1-N-X derivatives wherein X is —CH₂—Y (herein designated the 1-N-alkyl derivatives) or wherein X is

(herein designated the 1-N-acyl derivatives) are all well known in the art. U.S. Pat. No. 4,002,742 issued to Wright et al, describes the introduction of the 1-N-alkyl group on an aminoglycoside, a preferred procedure being the reaction of an acid addition salt of an aminoglycoside (e.g., 5-fluoro-5-deoxy or 5-epi-fluoro-5-deoxysisomicin sulfate) with one equivalent of a hydride donor reducing agent (e.g., sodium cyanoborohydride) and with at least one equivalent of an aldehyde (e.g. acetaldehyde) whereby is obtained the 1-N-alkylaminoglycoside (e.g. 5-fluoro-5-deoxy or 5-epi-fluoro-5-deoxy-1-N-ethylsisomicin).

Although fluorination is possible on a 1-N-acylaminoglycoside, the preferred method for preparing such compounds would be to introduce the 1-N-acyl moiety subsequent to fluorination. U.S. Pat. No. 4,029,882 describes methods for the introduction of the 1-N-acyl moiety. One such procedure is the reaction of a partially neutralized acid addition salt of an aminoglycoside (e.g., 5-fluoro-5-deoxy or 5-epi-fluoro-5-deoxysisomicin sulfate in water/methanol solution with triethylamine) with an acylating agent (e.g., N-(S-4-phthalimido-2-hydroxybutyryloxy)succinimide) followed by removal of the blocking group to obtain the 1-N-acylaminoglycoside (e.g., 5-fluoro-5-deoxy or 5-epi-fluoro-5-deoxy-1-N-(S-4-amino-2-hydroxybutyryl)sisomicin).

COMPOSITION-OF-MATTER ASPECT

In its composition-of-matter aspect, this invention relates to novel aminoglycosides and their pharmaceutically acceptable acid addition salts. Particularly, this invention relates to 5-fluoro-5-deoxy or 5-epi-fluoro-5-deoxy derivatives of 4,6-di-O-(aminoglycosyl)-1,3-diaminocyclitols or their 1-N-X derivatives and their pharmaceutically acceptable acid addition salts.

The 4,6-di-O-(aminoglycosyl)-1,3-diaminocyclitols having a 5-hydroxyl group whence our novel 5-fluoro-5-deoxy or 5-epi-fluoro-5-deoxy derivatives are produced, are selected from the group consisting of gentamicin A, gentamicin B, gentamicin B₁, gentamicin C₂ₐ, gentamicin C₂ᵦ, gentamicin X₂, verdamicin, tobramycin, Antibiotic G-418, Antibiotic 66-40B, Antibiotic 66-40D, Antibiotic JI-20A, Antibiotic JI-20B, Antibiotic G-52, kanamycin A, kanamycin B and 3',4'-dideoxykanamycin B and the 5-epi analogs of the foregoing. The 1-N-X derivatives of the foregoing which we contemplate are those wherein X is —CH₂Y or

wherein Y is a member selected from the group consisting of hydrogen, alkyl, alkenyl, cycloalkyl, cycloalkylalkyl, hydroxyalkyl, aminoalkyl, alkylaminoalkyl, aminohydroxyalkyl and alkylaminohydroxyalkyl, said Y having up to 4 carbon atoms and when substituted by both amino and hydroxyl groups, said groups are on different carbon atoms, and the pharmaceutically acceptable acid addition salts thereof.

Included among the substituents contemplated for the moiety Y in our novel compounds are hydrogen, straight and branched chain alkyl groups such as ethyl, n-propyl, isopropyl, n-butyl, isobutyl, tertiary-butyl and β-methylpropyl; alkenyl groups such as β-propenyl, β-methylpropenyl and β-butenyl; cycloalkyl groups such as cyclopropyl and cyclobutyl; cycloalkylalkyl group such as cyclopropylmethyl; hydroxy substituted straight and branched chain alkyl groups such as β- hydroxy-β-methylpropyl, δ-hydroxybutyl, β-hydroxypropyl, γ-hydroxypropyl and β-hydroxyethyl; amino substituted straight and branched chain alkyl groups such as β-aminopropyl, γ-aminopropyl and δ-aminobutyl; and mono-N-alkylated derivatives thereof such as the N-methyl, e.g. β-methylaminopropyl and δ-methylaminopropyl; amino and hydroxy disubstituted straight and branched chain alkyl groups such as β-hydroxy-δ-aminobutyl, β-hydroxy-γ-aminopropyl, and β-hydroxy-β-methyl-γ-aminopropyl.

Particularly valuable compounds of this invention are the following:
(a) 5-fluoro-5-deoxyverdamicin,
(b) 5-epi-fluoro-5-deoxyverdamicin,
(c) 5-fluoro-5-deoxytobramycin,
(d) 5-epi-fluoro-5-deoxytobramycin.

Particularly valuable 1-N-derivatives of the compounds of this invention are the following:
(a) the 1-N-X derivatives wherein X is —$CH_2Y$, Y being alkyl or aminoalkyl,
(b) 1-N-X derivatives wherein X is a

substituent selected from the group consisting of β-amino-α-hydroxypropionyl, γ-amino-α-hydroxybutyryl and δ-amino-α-hydroxyvaleryl.

Also included within the composition-of-matter aspect of this invention are the pharmaceutically acceptable acid addition salts of the 5-fluoro-5-deoxy and 5-epi-fluoro-5-deoxy-4,6-di-O-(aminoglycosyl)-1,3-diaminocyclitols or their 1-N-X derivatives described hereinabove. The salts which we contemplate are made according to known procedures, such as by neutralizing the free base with the appropriate acid, usually to about pH 5. Included among the pharmaceutically acceptable acid addition salts of this invention, are those derived from organic acids such as succinic acid, fumaric acid and maleic acid, or preferably, from inorganic acids such as hydrochloric, sulfuric, phosphoric and hydrobromic. The physical embodiments of the acid addition salts of this invention are characterized by being white solids which are soluble in water, sparingly soluble in most polar organic solvents and insoluble in most non-polar organic solvents.

In general, the 5-fluoro-5-deoxy and 5-epi-fluoro-5-deoxy-4,6-di-O-(aminoglycosyl)-1,3-diaminocyclitols or their 1-N-X derivatives of this invention and their pharmaceutically acceptable acid addition salts exhibit activity against a broad range of gram-positive and gram-negative pathogens. Advantageously, we have found that these compounds are active against many gentamicin/sisomicin resistant strains being comparable in spectrum to 1-N-ethylsisomicin, also known as netilmicin. The pathogenic types of bacteria against which our compounds exhibit activity are the gram-negative, such as *E. coli*, Klebsiella, Proteus, Providencia, Pseudomonas, Salmonella and Serratia; and the gram-positive, such as Staphylococcus, Streptococcus, and *B. subtilis*.

In addition to the foregoing, and more importantly, the compounds of our invention are less acutely toxic than their parents.

As discussed hereinabove, the 5-fluoro-5-deoxy and 5-epi-fluoro-5-deoxy-4,6-di-O-(aminoglycosyl)-1,3-diaminocyclitols or their 1-N-X derivatives of this invention and their non-toxic pharmaceutically acceptable acid addition salts exhibit broad activity against gram-positive and gram-negative pathogens. Thus, the compounds of our invention can be used alone, or in combination with other antibiotic agents to prevent the growth or reduce the number of bacteria in various environments. Their activity against gram-negative bacteria renders them useful for combating infection caused by species of *E. coli* and Pseudomonas. Additionally, our compounds would also have veterinary applications, particularly in the treatment of mastitis in cattle and Salmonella-induced diarrhea in domestic animals such as the dog and the cat. Our compounds may also be used to disinfect laboratory glassware dental and medical equipment contaminated with the gram-positive organism, *Staphylococcus aureus*, or other bacteria.

In general, the dosage administered of our compounds will be dependent upon the age and weight of the animal species being treated, the mode of administration and the type and severity of the bacterial infection being prevented or reduced.

The 5-fluoro-5-deoxy and 5-epi-fluoro-5-deoxy-4,6-di-O-(aminoglycosyl)-1,3-diaminocyclitols or their 1-N-X derivatives and the pharmaceutically acceptable acid addition salts thereof may be administered orally. They may also be applied topically in the form of ointments, both hydrophilic and hydrophobic, in the form of lotions which may be aqueous, non-aqueous, or other emulsion types, or in the form of creams or gels. Pharmaceutical carriers useful in the preparation of such formulations will include, for example, such substances as water, oils, fats, waxes, polyesters, alcohols, polyols and the like.

In general, the topical preparations will contain from about 0.1 to about 3.0 gms. of the compounds of this invention per 100 gms. of ointments, creams or lotion. The topical preparations are usually gently applied to lesions from about 2 to about 5 times a day.

For oral administration, the antibacterials of this invention may be compounded in the form of tablets, capsules, elixirs, or the like, or may even be admixed with animal feed. It is in these dosage forms that the antibacterials are most effective for treating bacterial infections of the gastrointestinal tract which infections cause diarrhea. They are also useful in pre- and post-operative gut sterilization.

The antibacterials of this invention may be utilized in liquid form such as solutions, suspensions and the like for otic and opthalmic use and may also be administered parenterally via intramuscular, intravenous, subcutaneous and intrasternal injection. The injectable solution, or suspension will usually be administered at from about 1 mg. to about 15 mgs. of antibacterial per kilogram of body weight per day divided into about 2 to about 4 doses. The precise dose depends on the stage and severity of the infection, the susceptibility of the infecting organism to the antibacterial and the individual characteristics of the animal species being treated.

The invention described hereinabove is illustrated in detail hereinbelow in the Preparations, Examples and Formulations and should not be construed as limiting the scope of our invention.

PREPARATION I

Diethylaminosulfur trifluoride (DAST)

To a solution of 40 ml. of sulfur tetrafluoride in 200 ml. trichlorofluoromethane, add dropwise a solution of 96 gm. (0.66 mole) of diethylaminotrimethylsilane in 100 ml. of trichlorofluoromethane, in the temperature range of −65° C. to −60° C. Let the reaction mixture warm to room temperature. Distill the reaction mixture to obtain about 86 gm. of DAST as a pale yellow liquid (b.p. 46°–47° C. at 10 mm).

PREPARATION II

A. 1,3,2',6',3''-Penta-N-Benzyloxycarbonylsisomicin

Dissolve 25 gms. of sisomicin and 13 gms. of sodium carbonate in 625 ml. of water. Stir the solution and add 100 ml. of benzylchloroformate at 25° C. Stir the mixture for 16 hours and then filter off the solid, washing thoroughly with water. Dry the solid in vacuo and then wash with hexane and air dry to obtain 62 gms. of 1,3,2',6',3''-penta-N-benzyloxycarbonylsisomicin; m.p.=165°–173° C.; $[\alpha]_D^{26}+96.2°$ ($CH_3OH$).

B. 1,3,2',6',3''-Penta-N-Benzyloxycarbonyl-5-Episisomicin

To a stirred solution of 2.3 gms. of 5-episisomicin and 10 gms. of sodium carbonate in 100 ml. of water at 0° C. add 10 ml. of benzylchloroformate. Stir the mixture at 0° C. for two hours and then at room temperature overnight. Add 200 ml. of ether and stir for one hour. Filter and wash the solid with water (500 ml.) and then with ether (500 ml.) to obtain 5.1 gm. of 1,3,2',6',3''-penta-N-benzyloxycarbonyl-5-episisomicin as white solid; m.p.=210° C.; $[\alpha]_D^{26}+95.2°$ ($CH_3OH$); Analysis $C_{59}H_{67}N_5O_{17}$.

PREPARATION III

A. 1,3,2',6'-Tetra-N-Benzyloxycarbonyl-3'',4''-N,O-Carbonylsisomicin

To a stirred solution of 5 gms. of the product of Preparation IIA in 50 ml. dimethylformamide, add 250 mg. of sodium hydride. Stir the reaction mixture under argon for 2 hours at room temperature. Filter and add 2 ml. glacial acetic acid to the filtrate. Concentrate the filtrate in vacuo and extract the residue with 200 ml. of chloroform (purified by passage through basic alumina). Wash the chloroform extracts with water and dry over sodium sulfate and evaporate to obtain 3.5 gm. of 1,3,2',6'-tetra-N-benzyloxycarbonyl-3'',4''-N-O-carbonylsisomicin, m.p. 210°–213° C., $[\alpha]_D^{26}+68.8°$ (c 0.22).

B. 1,3,2',6'-Tetra-N-Benzyloxycarbonyl-3'',4''-N,O-Carbonyl-5-Episisomicin

To a solution of 4 gms. of Preparation IIB in 75 ml. of dimethylformamide at 0° C., add 0.4 gms. of sodium hydride and stir the solution for 2 hours. Add 3 ml. of methanol and stir for 10 minutes. Evaporate the solution to dryness. Extract the product with chloroform (500 ml.) and wash twice with water (300 ml.). Dry the organic phase over sodium sulphate and evaporate the solvent under vacuum. Triturate the residual yellow foam with a small volume of ether to obtain 3 gm. of 1,3,2',6'-tetra-N-benzyloxycarbonyl-3'',4''-N,O-carbonyl-5-episisomicin as pale yellow solid; m.p.=250° C. (dec.).

PREPARATION IV

A. 1,3,2',6'-Tetra-N-Benzyloxycarbonyl-2''-O-Benzoyl-3'',4''-N,O-Carbonylsisomicin To a stirred solution of 3 gm. of the product of Preparation IIIA in 20 ml. of dry pyridine at 25° C. under an atmosphere of argon, add 1.7 ml. of benzoyl chloride over a 10 minute period. Stir at room temperature until all the starting material reacts (monitor by thin layer chromatography). Evaporate the mixture at room temperature under high vacuum; extract the solid residue with 100 ml. chloroform (previously passed through basic alumina). Wash the chloroform extracts with 5% aqueous sodium bicarbonate, water and then dry over sodium sulfate. Evaporate the solvent to obtain 2.8 gm. 1,3,2',6'-tetra-N-benzyloxycarbonyl-2''-O-benzoyl-3'',4''-N,O-carbonylsisomicin; m.p.=157°–160° C.; $[\alpha]_D^{26}+86°$ (c 0.2).

B. 1,3,2',6'-Tetra-N-Benzyloxycarbonyl-2''-O-Benzoyl-3'',4''-N,O-Carbonyl-5-Episisomicin To a solution of 2 gms. of the product of Preparation IIIB in 30 ml. of pyridine at 0° C. add 1 ml. of benzoyl chloride and stir for 2 hours. Evaporate the solution to dryness under high vacuum. Extract the residue with chloroform, dry over sodium sulphate and evaporate to dryness to give a pale yellow foam comprising the title compound (1.8 gm.).

PREPARATION V

1,3,2',6',3''-Penta-N-benzyloxycarbonyltobramycin

To a stirred solution of 4 gm. of tobramycin and 8 gm. of sodium carbonate in 50 ml. of water/methanol (1:1) at 0° C. add 16 ml. of benzyl chloroformate dropwise over a period of 15 minutes. Stir the reaction mixture at room temperature for three hours. Filter and wash the white solid with 200 ml. of water and then with 200 ml. of ether to obtain 9.0 gm. of 1,3,2',6',3''-penta-N-benzyloxycarbonyltobramycin; m.p. 240°–242° C.; $[\alpha]_D^{26}=+53.8°$ (c 0.3% MeOH).

PREPARATION VI

1,3,2',6',3''-penta-N-benzyloxycarbonyl-4',2'',4'',6''-tetra-O-benzoyltobramycin To a stirred solution of 4 gm. of 1,3,2',6',3''-penta-N-benzyloxycarbonyltobramycin in 80 ml. of pyridine at 0° C., add 3.5 ml. of benzoyl chloride under an atmosphere of argon. Stir the reaction mixture at 0° C. for 2 hours. Evaporate the reaction mixture to dryness under high vacuum (bath temperature 30°–40° C.) and extract the product into 200 ml. of chloroform, wash the organic phase with 200 ml. of water and then dry over 25 gms. of sodium sulfate. Evaporate the chloroform under vacuum. Triturate the pale yellow foam with a small amount of ether to obtain 5.5 gm. of 1,3,2',6',3''-penta-N-benzyloxycarbonyl-4',2'',4'',6''-tetra-O-benzoyltobramycin as a white solid; m.p.=120°–122° C.; $[\alpha]_D^{26}+40.3°$ (with 0.43% methanol).

PREPARATION VII

In a manner similar to Preparations IIA and B, IIIA and B, IVA and B, V and VI or by following the procedures set forth in U.S. Pat. No. 4,000,261, the starting compounds of this invention may be obtained, i.e. the N-protected-O-protected-4,6-di-O-(aminoglycosyl)-1,3-diaminocyclitols having a free 5-epihydroxyl or 5-hydroxyl group.

EXAMPLE 1

5-Fluoro-5-Deoxy and 5-Epi-Fluoro-5-Deoxy-N-Protected-O Protected-Aminoglycosides

A.

5-Epi-fluoro-5-deoxy-1,3,2',6'-tetra-N-benzyloxycarbonyl-2''-O-benzoyl-3'',4''-N,O-carbonylsisomicin To a stirred solution of 4 gm. of 1,3,2',6'-tetra-N-benzyloxycarbonyl-2''-O-benzoyl-3'',4''-N-O-carbonylsisomicin in 60 ml. of dry methylene chloride at $-78°$ C. under an atmosphere of argon, add 3 ml. (6 eq.) of diethylaminosulfur trifluoride. (DAST) Stir the reaction mixture at $-78°$ C. for two hours and then allow to warm to 0° C. Add 50 ml. of 5% sodium bicarbonate and separate the organic phase. Wash this organic phase with 50 ml. water and then dry over 25 gm sodium sulfate. Evaporate the methylene chloride under vacuum. Triturate the residual yellow foam with a small volume of ether to obtain 3.6 gm of 5-epi-fluoro-5-deoxy-1,3,2',6'-tetra-N-benzyloxycarbonyl-2''-O-benzoyl-3'',4''-N,O-carbonylsisomicin as a white solid; m.p.$=225°$ C.

B.

5-Epi-fluoro-5-deoxy-1,3,2',6'-tetra-N-benzyloxycarbonyl-2''-O-benzoyl-3'',4''-N,O-carbonylverdamicin To a stirred solution of 3 gm of 1,3,2',6'-tetra-N-benzyloxycarbonyl-2''-O-benzoyl-3'',4''-N,O-carbonylverdamicin in 50 ml of dry methylene chloride at $-78°$ C., add 2.3 ml. of DAST. Stir the reaction mixture at $-78°$ C. under an atmosphere of argon for 2 hours. Allow the solution to warm to 0° C. Add 40 ml. of 5% sodium bicarbonate and separate the organic phase. Wash this organic phase with 40 ml. water and dry over sodium sulfate. Evaporate the methylene chloride under vacuum. Triturate the residual yellow foam with a small volume of ether to obtain 2.3 gm of 5-epi-fluoro-5-deoxy-1,3,2',6'-tetra-N-benzyloxycarbonyl-2''-O-benzoyl-3'',4''-N,O-carbonylverdamicin; m.p.$=104°-106°$ C.; $[\alpha]_D^{26}+95.2°$ (methanol).

C.

5-Epi-fluoro-5-deoxy-1-N-ethyl-1,3,2',6',-tetra-N-benzyloxycarbonyl-2''-O-benzoyl-3'',4''-N,O-carbonylsisomicin To a stirred solution of 4.5 gm. of 1-N-ethyl-1,3,2',6'-tetra-N-benzyloxycarbonyl-2''-O-benzoyl-3'',4''-N,O-carbonylsisomicin in 60 ml. of dry methylene chloride at $-78°$ C. under an atmosphere of argon, add 3.4 ml. of DAST. Continue to stir the reaction mixture at $-78°$ C. for two hours and then allow to warm to 0° C. Add 50 ml. of 5% sodium bicarbonate and separate the organic phase. Wash this organic phase with 50 ml. of water and then dry over sodium sulfate. Evaporate the methylene chloride under vacuum. Triturate the residual yellow foam with a small volume of ether to obtain 4.1 gm. of 5-epi-fluoro-5-deoxy-1-N-ethyl-1,3,2',6'-tetra-N-benzyloxycarbonyl-2''-O-benzoyl-3'',4''-N,O-carbonylsisomicin; m.p. $85°-90°$ C.; $[\alpha]_D^{26}+111.4°$ (methanol).

D.

5-Epi-fluoro-5-deoxy-1,3,2',6',3''-penta-N-benzyloxycarbonyl-4',2'',4'',6''-tetra-O-benzoyltobramycin To a stirred solution of 2 gm. of 1,3,2',6',3''-penta-N-benzyloxycarbonyl-4',2'',4'',6''-tetra-O-benzoyltobramycin in 25 ml. of methylene chloride at $-78°$ C. under an atmosphere of argon add 1 ml. of DAST. Stir the reaction mixture at $-78°$ C. for two hours and then allow to warm to 0° C. and continue to stir at 0° C. for 8 hours. Add 50 ml. of sodium carbonate and separate the organic phase. Wash the organic phase with 50 ml. of water and then dry over 25 gm. of sodium sulfate. Evaporate the methylene chloride under vacuum. Triturate the residual yellow foam with a small volume of ether to obtain 1.9 gm. of 5-epi-fluoro-5-deoxy-1,3,2',6',3''-penta-N-benzyloxycarbonyl-4',2'',4'',6''-tetra-O-benzoyltobramycin as a pale yellow solid; m.p.$=100°-103°$ C.; $[\alpha]_D^{26}+72.1°$ (c 0.34% methanol).

E.

5-Fluoro-5-Deoxy-1,3,2',6'-Tetra-N-Benzyloxycarbonyl-2''-O-Benzoyl-3'',4''-N,O-Carbonylsisomicin Dissolve the product of Preparation IVB in methylene chloride (30 ml.) and cool to $-78°$ C. Add DAST (1 ml.) and stir at $-78°$ C. for one hour, and then allow to warm to 0° C. and continue stirring for 16 hours. Add 50 ml. of aqueous sodium carbonate (10%) and separate the organic phase. Wash this organic phase with 50 ml. of water and then dry over 25 gms. of sodium sulphate. Evaporate the methylene chloride under vacuum to give a yellow foam (1.4 gms.) comprising the title compound.

EXAMPLE 2

5-Fluoro-5-Deoxy and 5-Epi-Fluoro-5-Deoxy Aminoglycosides

A. 5-Epi-fluoro-5-deoxysisomicin

To a solution of 4 gm. of 5-epi-fluoro-5-deoxy-1,3,2',6'-tetra-N-benzyloxycarbonyl-2''-O-benzoyl-3'',4''-N,O-carbonylsisomicin in 5 ml. of tetrahydrofuran and 60 ml. liquid ammonia. slowly add 2 gm. of sodium with stirring. Continue to stir for two hours, then add 15 ml. of methanol dropwise and allow the ammonia to evaporate by warming to room temperature overnight. Dissolve the resultant residue in 10 ml. 5% sodium hydroxide, and heat at 100° C. for two hours under an atmosphere or argon. Cool and pass the solution through IRC-50 (H+) resin. Wash the resin with water and elute the product with 100 ml. of 1 N ammonium hydroxide. Concentrate the ammonium hydroxide eluates to a residue comprising 5-epi-fluoro-5-deoxysisomicin. Purify the product by chromatographing on a silica gel column eluting with the lower phase of a chloroform:methanol:15% ammonium hydroxide (2:1:1) solvent system. Combine the like eluates as determined by thin layer chromatography and lyophilize to a residue to obtain 750 mg. 5-epi-fluoro-5-deoxysisomicin as a white solid; m.p. 100° C.$-$102° C.; $[\alpha]_D^{26}+200°$ (MeOH); PMR (100 MHz) (D$_2$O), 5.1 (1H,d,J$=$57.0 Hz,5-H), 5.13(1H,d,J$=$2.5 Hz,1'-H), 5.03(1H,d,J$=$4.0 Hz,1''-H), 4.88(1H,br. s,4'-H), 3.85(1H,d,J$=$12.5 Hz,5$_e$''-H), 3.36(1H,d,J$=$12.5 Hz,5$_a$''-H), 2.56(1H,d,J$=$10.5 Hz,3''-H), 2.47(3H,s,3''-N-CH$_3$), 1.17(3H,s,4'-C-CH$_3$).

B. 5-Epi-fluoro-5-deoxyverdamicin

To a solution of 2.2 gm. of 5-epi-fluoro-5-deoxy-1,3,2',6'-tetra-N-benzyloxycarbonyl-2''-O-benzoyl-3'',4''-N,O-carbonylverdamicin in 5 ml. of tetrahydrofuran and 60 ml. ammonia, slowly add 2 gms. of sodium with stirring. Continue to stir for two hours, then add 10 ml. of methanol dropwise to the stirred mixture and allow the ammonia to evaporate by warming to room temperature overnight. Dissolve the resultant residue in 10 ml. of 5% sodium hydroxide and heat at 100° C. for two hours under argon. Cool and pass the solution through IRC-50 (H+) resin. Wash the resin well with water and elute the product with 100 ml. of 1 N, NH$_4$OH. Concentrate the NH$_4$OH eluates to a residue comprising 5-epi-fluoro-5-deoxyverdamicin. Purify the product by chromatographing on a silica gel column with the lower phase of chloroform:methanol:10% NH$_4$OH (2:1:1) solvent system. Combine the like eluates as determined by thin layer chromatography and lyophilize to a residue to obtain 360 mg. of 5-epi-fluoro-5-deoxyverdamicin as a white solid; m.p.=92°–95° C.; $[\alpha]_D^{26}+193.4°$ (MeOH); PMR (80 MHz) (D$_2$O) δ5.13(1H,d,J=54 Hz,5-H), 5.13(1H,d,J=2.5 Hz, 1'-H), 5.01(1H,d,J=4 Hz,1''-H), 4.91(1H,br. s,4'-H), 3.81(1H,d,J=12.5 Hz, 5$_e$''-H), 3.42 (1H,d,J=12.5 Hz,5$_a$''-H), 2.62 (1H,d,J=10.5 Hz,3''-H), 2.55 (3H,s,3''-N-CH$_3$), 1.28(3H,s,4''-C-CH$_3$), 1.22 (3H,d,J=7 Hz,6'-CH-CH$_3$).

C. 5-Epi-fluoro-5-deoxy-1-N-Ethylsisomicin

To a solution of 2 gm. of 1-N-ethyl-5-epi-fluoro-5-deoxy-1,3,2',6'-tetra-N-benzyloxycarbonyl-2''-O-benzoyl-3'',4''-N,O-carbonylsisomicin in 5 ml. of tetrahydrofuran and 50 ml. ammonia, slowly add 2 gm. of sodium with stirring and continue to stir for two hours. Add 15 ml. methanol dropwise to the stirred mixture and allow ammonia to evaporate at room temperature overnight. Dissolve the resultant residue in 10 ml. of 5% sodium hydroxide and heat at 100° C. for two hours under an atmosphere of argon. Cool and pass the solution through IRC-50 (H+) resin. Wash the resin well with water and elute the product with 100 ml. 1 N ammonium hydroxide. Concentrate the ammonium hydroxide eluate to a residue comprising 5-epi-fluoro-5-deoxy-1-N-ethylsisomicin. Purify the product by chromatographing on a silica gel column eluting with the lower phase of chloroform:methanol:10% ammonia hydroxide (2:1:1) solvent system. Combine the like eluates as determined by thin layer chromatography and lyophilize to a residue to obtain 225 mg. of 5-epi-fluoro-5-deoxy-1-N-ethylsisomicin as a white solid; m.p. 85°–88° C.; $[\alpha]_D^{26}+159.3°$ (MeOH); PMR (80 MHz) (D$_2$O) δ 5.03(1H,d,J=55 Hz,5-H), 4.99 (1H,d,J=2.5 Hz,1'-H), 4.83(1H,d,J=4.0 Hz,1''-H), 4.65 (1H,br. s,4'-H), 3.65(1H,d,J=12 Hz,5$_e$''-H), 3.20(1H,d,J=12 Hz,5$_a$''-H), 2.40(1H,d,J=10 Hz,3''-H), 2.32(3H,s,3''-N-CH$_3$), 1.05(3H,s,4''-C-CH$_3$), 0.89(3H,t,J=7 Hz,1 N-CH$_2$-CH$_3$).

D. 5-Epi-fluoro-5-deoxytobramycin

To a solution of 1.8 gm. of 5-epi-fluoro-5-deoxy-1,3,2',6',3''-penta-N-benzyloxycarbonyl-4',2'',4'',6''-tetra-O-benzoyltobramycin in 5 ml. of tetrahydrofuran and 30 ml. ammonia, slowly add 2 gm. of sodium with stirring and continue to stir for two hours. Add 15 ml. of methanol dropwise and allow the ammonia to evaporate by warming to room temperature overnight. Dissolve the resultant residue in 10 ml. of water and pass through IRC-50 (H+) resin. Wash the resin well with water and elute the product with 100 ml. 1 N ammonium hydroxide. Concentrate the ammonium hydroxide eluate to a residue comprising 5-epi-fluoro-5-deoxytobramycin. Purify the product by chromatographing on a silica gel column eluting with chloroform:methanol:10% ammonium hydroxide (1:2:1) solvent system. Combine the like eluates as determined by thin layer chromatography and lyophilize to a residue to obtain 335 mg. of 5-epi-fluoro-5-deoxytobramycin as a white solid; m.p. 150°–154° C.; PMR (D$_2$O) 80 MHz, 5.35 (1H,d,J=55.5 Hz,5-H), 5.08 (1H,d,J=4.0 Hz,1'-H), 4.95(1H,d,J=3.8 Hz,1''-H),

E. 5-Fluoro-5-Deoxysisomicin

Dissolve the product of Example 1E in 5 ml. of tetrahydrofuran and 30 ml. ammonia. Slowly add 2 gms. of sodium with stirring and continue to stir for 2 hours. Add 15 ml. of methanol dropwise and allow the ammonia to evaporate by warming to room temperature overnight. Dissolve the resultant residue in 10% aqueous sodium hydroxide (50 ml.) and reflux for two hours under an atmosphere of argon. Cool and pass the solution through IRC-50 (H+) resin. Wash the resin well with water and elute the product with 100 ml. of 1 N ammonium hydroxide. Concentrate the ammonium hydroxide eluate to a residue comprising 5-fluoro-5-deoxysisomicin. Purify the product by chromatographing on a silica gel column eluting with the lower phase of chloroform:methanol:15% ammonium hydroxide (2:1:1) solvent system. Combine the like eluate as determined by thin layer chromatography and lyophilize to a residue to obtain 338 mg. of 5-fluoro-5-deoxysisomicin as a white solid; m.p. 90° C.; $[\alpha]_D^{26}+188.1°$ (MeOH); pmr (80 MHz) (D$_2$O) δ5.25 (1H, d, J=2.5 Hz,1'-H), 5.05 (1H, d, J=4.0 Hz,1''-H), 4.85 (1H, broad singlet, 4'-H), 4.50 (1H, doublet, J=50.0 Hz,5-H-F), 3.75 (1H, doublet, J=12.5 Hz,5''$_e$-H), 3.30 (1H, doublet, J=12.5 Hz,5''$_{ax}$-H), 2.55 (1H, doublet, J=11.0 Hz,3''-H), 2.5 (3H, singlet, 3''-N-CH$_3$), 1.2 (3H, singlet, 4''-C-CH$_3$).

F. 5-Epi-Fluoro-5-Deoxy and 5-Fluoro-5-Deoxy-4,6-Di-O-(Aminoglycosyl)-1,3-Diaminocyclitols and 1-N-Ethyl Derivatives In a manner similar to that described in Example 1 (A-E), treat each of the following N,O-protected aminoglycosides having a free 5-hydroxyl group or their 5-epimers:

(a) 1,3,2',3''-tetra-N-benzyloxycarbonyl-3',4',6',2'',4''-penta-O-benzoylgentamicin A, (b) 1,3,2',6',3''-penta-N-benzyloxycarbonyl-2'',4''-di-O-benzoyl-Antibiotic 66-40B, (c) 1,3,2',6',3''-penta-N-benzyloxycarbonyl-2'',4''-di-O-benzoyl Antibiotic 66-40D, (d) 1,3,6',3''-tetra-N-benzyloxycarbonyl-2',3',4',2'',4'',6''-hexa-O-benzoylkanamycin A, (e) 1,3,2',6',3''-penta-N-benzyloxycarbonyl-3',4',2'',4'',6''-penta-O-benzoylkanamycin B, (f) 1,3,2',6',3''-penta-N-benzyloxycarbonyl-2'',4'',6''-tri-O-benzoyl-3',4'-dideoxykanamycin B, (g) the 1,3,2',6'-tetra-N-benzyloxycarbonyl-2''-O-benzoyl-3'',4''-N,O-carbonyl derivatives of gentamicins C$_1$, C$_{1a}$, C$_2$, C$_{2a}$, C$_{2b}$ and Antibiotic G-52, (h) the 1,3,6'-tri-N-benzyloxycarbonyl-2',3',4',2''-tetra-O-benzoyl-3'',4''-N,O-carbonyl derivatives of gentamicin B and B$_1$, (i) the 1,3,2',6'-tetra-N-benzyloxycarbonyl-3',4'-O-benzylidene-2''-O-benzoyl-3'',4''-N,O-carbonyl derivatives of Antibiotics JI-20A and JI-20B, (j) the 1,3,2'-tri-N-benzyloxycarbonyl-3',2''-di-O-benzoyl-4',6'-O-cyclohexylidene-3'',4''-N,O-carbonyl derivatives of gentamicin $X_2$ and Antibiotic G-418, and the 1-N-ethyl derivatives of the foregoing.

Isolate and purify the resultant respective products in a manner similar to that described in Example 2 (A-E) to obtain the 5-epi-fluoro-5-deoxy derivatives of gentamicin A, Antibiotics 66-40B, 66-40D, kanamycin A, kanamycin B, 3',4'-dideoxykanamycin B, gentamicins $C_1$, $C_{1a}$, $C_2$, $C_{2a}$, $C_{2b}$, Antibiotic G-52, gentamicins B, $B_1$, Antibiotics JI-20A, JI-20B, gntamicin $X_2$ and Antibiotic G-418, and the 1-N-ethyl derivatives of each of the foregoing, respectively.

EXAMPLE 3

5-Fluoro-5-Deoxy and 5-Epi-Fluoro-5-Deoxy-1-N-Acylaminoglycosides

A. 5-Fluoro-5-Deoxy or 5-Epi-Fluoro-5-Deoxy-1-N-(S-4-Phthalimido-2-Hydroxybutyryl)verdamicin Dissolve 5.00 gm. of 5-fluoro-5-deoxy or 5-epi-fluoro-5-deoxyverdamicin sulfate in 50 ml. of water and add 25 ml. of methanol. Add 0.50 ml. of triethylamine and stir for 10 minutes. Add a solution containing 2.5 gm. of N-(S-4-phthalimido-2-hydroxybutyryloxy)-succinimide in 10 ml. of dimethylformamide dropwise with stirring. Stir the mixture overnight at ambient temperature, then concentrate to a residue in vacuo. Chromatograph the residue over 160 gm. of silica gel, eluting with the lower phase of a chloroform:methanol:concentrated ammonium hydroxide (1:1:1) solvent mixture. Combine and evaporate fractions containing the major component of the reaction (determined by TLC on silica gel plates) and obtain thereby the compound of this example as a white amorphous solid.

B. 5-Fluoro-5-Deoxy or 5-Epi-Fluoro-5-Deoxy-1-N-(S-4-Amino-2-Hydroxybutyryl)verdamicin Dissolve 5-fluoro-5-deoxy or 5-epi-fluoro-5-deoxy-1-N-(S-4-phthalimido-2-hydroxybutyryl)verdamicin from Example 3A in 40 ml. of ethanol and add 0.2 gm. of hydrazine hydrate. Reflux the solution for 3 hours, then evaporate to dryness in vacuo. Chromatograph the residue over 160 gm. of silica gel, eluting with the lower phase of a chloroform:methanol:concentrated ammonium hydroxide (1:1:1) solvent mixture. Combine and evaporate fractions containing the major component of the reaction (determined by TLC on silica gel plates) and obtain as a white amorphous solid, 5-fluoro-5-deoxy or 5-epi-fluoro-5-deoxy-1-N-(S-4-amino-2-hydroxybutyryl)verdamicin.

C. 5-Fluoro-5-Deoxy or 5-Epi-Fluoro-5-Deoxy-1-N-(S-4-Amino-2-Hydroxybutyryl) aminoglycosides In a similar manner, subject to the process described in Example 3A and 3B an equivalent quantity of the following antibiotics:
(a) 5-fluoro-5-deoxy or 5-epi-fluoro-5-deoxysisomicin,
(c) 5-fluoro-5-deoxy or 5-epi-fluoro-5-deoxy Antibiotic G-52,
(c) 5-fluoro-5-deoxy or 5-epi-fluoro-5-deoxy Antibiotic 66-40B, and
(d) 5-fluoro-5-deoxy or 5-epi-fluoro-5-deoxy Antibiotic 66-40D.

Isolate the respective products in the manner described in Example 3A and 3B and obtain thereby the following:
5-fluoro-5-deoxy or 5-epi-fluoro-5-deoxy-1-N-(S-4-amino-2-hydroxybutyryl)sisomicin,
5-fluoro-5-deoxy or 5-epi-fluoro-5-deoxy-1-N-(S-4-amino-2-hydroxybutyryl)-Antibiotic G-52,
5-fluoro-5-deoxy or 5-epi-fluoro-5-deoxy-1-N-(S-4-amino-2-hydroxybutyryl)-Antibiotic 66-40B, and
5-fluoro-5-deoxy or 5-epi-fluoro-5-deoxy-1N-(S-4-amino-2-hydroxybutyryl)-Antibiotic 66-40D.

D. 5-Fluoro-5-Deoxy or 5-Epi-Fluoro-5-Deoxy-1-N-(S-3-Amino-2-Hydroxypropionyl)Aminoglycosides In an analogous manner, by substituting in Example 3A an equivalent quantity of N-(S-3-phthalimido-2-hydroxypropionyloxy)succinimide for N-(S-4-phthalimido-2-hydroxybutyryloxy)succinimide and by treating the above-named 5-fluoro-5-deoxy or 5-epi-fluoro-5-deoxy derivatives of verdamicin and the compounds of (Example 3C a–d) to the process of Example 3A and 3B, the following products may be obtained:
5-fluoro-5-deoxy or 5-epi-fluoro-5-deoxy-1-N-(S-3-amino-2-hydroxypropionyl)sisomicin,
5-fluoro-5-deoxy or 5-epi-fluoro-5-deoxy-1-N-(S-3-amino-2-hydroxypropionyl)-Antibiotic G-52,
5-fluoro-5-deoxy or 5-epi-fluoro-5-deoxy-1-N-(S-3-amino-2-hydroxypropionyl)-Antibiotic 66-40B, and
5-fluoro-5-deoxy or 5-epi-fluoro-5-deoxy-1-N-(S-3-amino-2-hydroxypropionyl)-Antibiotic 66-40D.

F. 5-Fluoro-5-Deoxy or 5-Epi-Fluoro-5-Deoxy-1-N-(S-4-Benzyloxy)carbonylamino-2-hydroxybutyryl)Gentamicin B Dissolve 3.39 gm. of 5-fluoro-5-deoxy or 5-epi-fluoro-5-deoxygentamicin B sulfate in 48.4 ml. of water and dilute with 23.7 ml. of methanol. Add 0.7 of triethylamine dropwise with stirring. Dissolve 1.67 gm. of N-(S-4-benzyloxycarbonylamino-2-hydroxybutyryloxy) succinimide in dimethylformamide and add the solution dropwise with stirring to the antibiotic solution. Stir the resulting solution at room temperature for 18 hours then concentrate to a residue in vacuo. Dissolve the residue in water and treat with dilute barium hydroxide solution with stirring until the pH reaches 8.0. Remove the precipitated barium sulfate by filtration using a filter aid. Wash the precipitate with water, combine the filtrate and washings and concentrate to dryness in vacuo. Chromatograph the residue on a column containing 600 gm. of silica gel using the lower phase of a solvent system consisting of chloroform, methanol, ammonium hydroxide (1:1:1) as the eluant. Pool the appropriate fractions as determined by thin layer chromatography and PMR analysis and concentrate said fractions to dryness and obtain 5-fluoro-5-deoxy or 5-epi-fluoro-5-deoxy-1-N-(S-4-benzyloxycarbonylamino-2-hydroxybutyryl)gentamicin B as an amorphous solid.

G. 5-Fluoro-5-Deoxy or 5-Epi-Fluoro-5-Deoxy-1-N-(S-4-Amino-2-Hydroxybutyryl)Gentamicin B Dissolve the product of step F in a mixture consisting of 20 ml of water and 8 ml of methanol. Hydrogenate the product in the presence of 60 mg of 5% palladium-on-carbon at 50 psi and room temperature for 3 hours.

Remove the catalyst by filtration through a filter aid. Wash the filter pad with water and combine the filtrate and washings. Concentrate the combined filtrate and washings to dryness in vacuo. Chromatograph the residue on a silica gel column containing 10 gm. of silica gel using the lower phase of a solution consisting of chloroform, methanol, ammonium hydroxide (2:1:1) as the eluant. Fractions containing the most polar component are pooled, concentrated and lyophilized to give 5-fluoro-5-deoxy or5-epi-fluoro-5-deoxy-1-N-(S-4-amino-2-hydroxybutyryl)gentamicin B.

H. 5-Fluoro-5-Deoxy or 5-Epi-Fluoro-5-Deoxy-1-N-(S-4-Amino-2-Hydroxybutyryl)Aminoglycosides In a manner similar to Example 3F and 3G, treat an equivalent quantity of the following 5-fluoro-5-deoxy or 5-epi-fluoro-5-deoxyaminoglycosides.

(a) 5-fluoro-5-deoxy or 5-epi-fluoro-5-deoxygentamicin A,
(b) 5-fluoro-5-deoxy or 5-epi-fluoro-5-deoxygentamicin $B_1$,
(c) 5-fluoro-5-deoxy or 5-epi-fluoro-5-deoxygentamicin $C_1$,
(d) 5-fluoro-5-deoxy or 5-epi-fluoro-5-deoxygentamicin $C_{1a}$,
(e) 5-fluoro-5-deoxy or 5-epi-fluoro-5-deoxygentamicin $C_2$,
(f) 5-fluoro-5-deoxy or 5-epi-fluoro-5-deoxygentamicin $C_{2a}$,
(g) 5-fluoro-5-deoxy or 5-epi-fluoro-5-deoxygentamicin $C_{2b}$,
(h) 5-fluoro-5-deoxy or 5-epi-fluoro-5-deoxygentamicin $X_2$,
(i) 5-fluoro-5-deoxy or 5-epi-fluoro-5-deoxytobramycin,
(j) 5-fluoro-5-deoxy or 5-epi-fluoro-5-deoxy Antibiotic G-418,
(k) 5-fluoro-5-deoxy or 5-epi-fluoro-5-deoxy Antibiotic JI-20A,
(l) 5-fluoro-5-deoxy or 5-epi-fluoro-5-deoxy Antibiotic JI-20B,
(m) 5-fluoro-5-deoxy or 5-epi-fluoro-5-deoxykanamycin A,
(n) 5-fluoro-5-deoxy or 5-epi-fluoro-5-deoxykanamycin B,
(o) 5-fluoro-5-deoxy or 5-epi-fluoro-5-deoxy-3',4'-dideoxykanamycin B.

Isolate the respective products in the manner described in Example 3F and 3G and obtain the following:
5-fluoro-5-deoxy or 5-epi-fluoro-5-fluoro-5-deoxy-1-N-(S-4-amino-2-hydroxybutyryl)gentamicin A,
5-fluoro-5-deoxy or 5-epi-fluoro-5-deoxy-1-N-(S-4-amino-2-hydroxybutyryl)gentamicin $B_1$,
5-fluoro-5-deoxy or 5-epi-fluoro-5-deoxy-1-N-(S-4-amino-2-hydroxybutyryl)gentamicin $C_1$,
5-fluoro-5-deoxy or 5-epi-fluoro-5-deoxy-1-N-(S-4-amino-2-hydroxybutyryl)gentamicin $C_{1a}$,
5-fluoro-5-deoxy or 5-epi-fluoro-5-deoxy-1-N-(S-4-amino-2-hydroxybutyryl)gentamicin $C_2$,
5-fluoro-5-deoxy or 5-epi-fluoro-5-deoxy-1-N-(S-4-amino-2-hydroxybutyryl)gentamicin $C_{2a}$,
5-fluoro-5-deoxy or 5-epi-fluoro-5-deoxy-1-N-(S-4-amino-2-hydroxybutyryl)gentamicin $C_{2b}$,
5-fluoro-5-deoxy or 5-epi-fluoro-5-deoxy-1-N-(S-4-amino-2-hydroxybutyryl)gentamicin $X_2$,
5-fluoro-5-deoxy or 5-epi-fluoro-5-deoxy-1-N-(S-4-amino-2-hydroxybutyryl)tobramycin,
5-fluoro-5-deoxy or 5-epi-fluoro-5-deoxy-1-N-(S-4-amino-2-hydroxybutyryl)-Antibiotic G-418,
5-fluoro-5-deoxy or 5-epi-5-deoxy-1-N-(S-4-amino-2-hydroxybutyryl)-Antibiotic JI-20A,
5-fluoro-5-deoxy or 5-epi-fluoro-5-deoxy-1-N-(S-4-amino-2-hydroxybutyryl)-Antibiotic JI-20B,
5-fluoro-5-deoxy or 5-epi-fluoro-5-deoxy-1-N-(S-4-amino-2-hydroxybutyryl)kanamycin A,
5-fluoro-5-deoxy or 5-epi-fluoro-5-deoxy-1-N-(S-4-amino-2-hydroxybutyryl)kanamycin B,
5-fluoro-5-deoxy or 5-epi-fluoro-5-deoxy-1-N-(S-4-amino-2-hydroxybutyryl)3',4'-dideoxykanamycin B.

I. 5-Fluoro-5-Deoxy or 5-Epi-Fluoro-5-Deoxy-1-N-(S-3-Amino-2-Hydroxypropionyl)Aminoglycosides In an analogous manner, by substituting in Example 3F an equivalent quantity of N-(S-3-benzyloxycarbonylamino-2-hydroxypropionyl)succinimide for N-(S-4-benzyloxycarbonylamino-2-hydroxybutyryl)succinimide, and by treating 5-fluoro-5-deoxy or 5-epi-fluoro-5-deoxygentamicin B and the compounds of Example 3H (a-o) to the process of Example 3F and 3G, the following products may be obtained:
5-fluoro-5-deoxy or 5-epi-fluoro-5-deoxy-1-N-(S-3-amino-2-hydroxypropionyl)gentamicin B,
5-fluoro-5-deoxy or 5-epi-fluoro-5-deoxy-1-N-(S-3-amino-2-hydroxypropionyl)gentamicin A,
5-fluoro-5-deoxy or 5-epi-fluoro-5-deoxy-1-N-(S-3-amino-2-hydroxypropionyl)gentamicin $B_1$,
5-fluoro-5-deoxy or 5-epi-fluoro-5-deoxy-1-N-(S-3-amino-2-hydroxypropionyl)gentamicin $C_1$,
5-fluoro-5-deoxy or 5-epi-fluoro-5-deoxy-1-N-(S-3-amino-2-hydroxypropionyl)gentamicin $C_{1a}$,
5-fluoro-5-deoxy or 5-epi-fluoro-5-deoxy-1-N-(S-3-amino-2-hydroxypropionyl)gentamicin $C_2$,
5-fluoro-5-deoxy or 5-epi-fluoro-5-deoxy-1-N-(S-3-amino-2-hydroxypropionyl)gentamicin $C_{2b}$,
5-fluoro-5-deoxy or 5-epi-fluoro-5-deoxy-1-N-(S-3-amino-2-hydroxypropionyl)gentamicin $X_2$,
5-fluoro-5-deoxy or 5-epi-fluoro-5-deoxy-1-N-(S-3-amino-2-hydroxypropionyl)tobramycin,
5-fluoro-5-deoxy or 5-epi-fluoro-5-deoxy-1-N-(S-3-amino-2-hydroxypropionyl)-Antibiotic G-418,
5-fluoro-5-deoxy or 5-epi-fluoro-5-deoxy-1-N-(S-3-amino-2-hydroxypropionyl)-Antibiotic JI-20A,
5-fluoro-5-deoxy or 5-epi-fluoro-5-deoxy-1-N-(S-3-amino-2-hydroxypropionyl)-Antibiotic JI-20B,
5-fluoro-5-deoxy or 5-epi-fluoro-5-deoxy-1-N-(S-3-amino-2-hydroxypropionyl)kanamycin A,
5-fluoro-5-deoxy or 5-epi-fluoro-5-deoxy-1-N-(S-3-amino-2-hydroxypropionyl)kanamycin B,
5-fluoro-5-deoxy or 5-epi-fluoro-5-deoxy-1-N-(S-3-amino-2-hydroxypropionyl)-3',4'-dideoxykanamycin B.

FORMULATIONS

Formulation I

| Tablet | 10 mg. Tab. | 25 mg. Tab. | 100 mg. Tab. |
|---|---|---|---|
| 5-epi-fluoro-5-deoxyverdamicin | 10.50*mg. | 26.25*mg. | 105.00*mg. |
| Lactose, impalpable powder | 197.50 mg. | 171.25 mg. | 126.00 mg. |
| Corn Starch | 25.00 mg. | 25.00 mg | 35.00 mg. |
| Polyvinylpyrrolidone | 7.50 mg. | 7.50 mg. | 7.50 mg. |
| Magnesium Stearate | 2.50 mg. | 2.50 mg. | 3.50 mg. |

| Tablet | 10 mg. Tab. | 25 mg. Tab. | 100 mg. Tab. |
|---|---|---|---|
|  | 243.00 mg. | 232.50 mg. | 277.00 mg. |

*5% excess

Procedure

Prepare a slurry consisting of the 5-epi-fluoro-5-deoxyverdamicin, lactose and polyvinyl pyrrolidone. Spray dry the slurry. Add corn starch and magnesium stearate. Mix and compress into tablets on a suitable press to the specified weight.

Formulation 2

| Ointment | |
|---|---|
| 5-epi-fluoro-5-deoxyverdamicin | 1.0 gm. |
| Methyl paraben USP | 0.5 gm. |
| Propyl paraben USP | 0.1 gm. |
| Petrolatum | to 1000 gm. |

Procedure (1) Melt the petrolatum.
(2) Mix the 5-epi-fluoro-5-deoxyverdamicin, methyl paraben and propyl paraben with about 10% of molten petrolatum and make a slurry. Mill the slurry and add to the balance of the petrolatum. Cool to room temperature with agitation.

Formulation 3

| Injectable Solution | Per 2.0 ml. Vial | Per 50 Liters |
|---|---|---|
| 5-epi-fluoro-5-deoxy-verdamicin | 84* mgs. | 2100* gms. |
| Methylparaben, USP | 3.6 mgs. | 90.0 gms. |
| Propylparaben, USP | 0.4 mgs. | 10.0 gms. |
| Sodium bisulfite, USP | 6.4 mgs. | 160.0 gms. |
| Disodium Ethylenediamine tetraacetate dihydrate, R.G. | 0.2 mgs. | 5.0 gms. |
| Water, USP q.s. | 2.0 ml. | 50.0 liters |

*Includes a 5% manufacturing overcharge

Procedure: For a 50.0 Liter Batch

Charge approximately 35 liters of water for injection to a suitable stainless steel jacketed vessel and heat to about 70° C. Charge the methylparaben and propylparaben to the heated water for injection and dissolve with agitation. When the parabens are completely dissolved, cool the contents of the tank to 25°–30° C. by circulating cold water through the tank jacket. Sparge the solution with nitrogen gas for at least 10 minutes and keep covered with nitrogen during subsequent processing. Charge and dissolve the disodium EDTA and sodium bisulfite. Charge and dissolve the 5-epi-fluoro-5-deoxyverdamicin. Bring the batch volume up to 50.0 liters with water for injection and agitate until homogeneous.

Under sterile conditions, filter the solution through a suitable bacteria retentive filter collecting the filtrate in a filling tank.

Fill the filtrate aseptically into sterile pyrogen-free multiple dose vials, stopper and seal.

We claim:

1. The process of preparing 5-fluoro-5-deoxy or 5-epi-fluoro-5-deoxy derivatives of 4,6-di-O-(aminoglycosyl)-1,3-diaminocyclitols or their 1-N-X derivatives, wherein X is 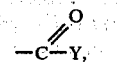 $CH_2Y$ or

wherein Y is a member selected from the group consisting of hydrogen, alkyl, alkenyl, cycloalkyl, cycloalkylalkyl, hydroxyalkyl, aminoalkyl, alkylaminoalkyl, aminohydroxyalkyl and alkylaminohyroxyalkyl, said Y having up to 4 carbon atoms and when substituted by both amino and hydroxy groups, said groups are on different carbon atoms;

which comprises the reaction of dialkylaminosulfur trifluoride with a 4,6-di-O-(aminoglycosyl)-1,3-diaminocyclitol or its 1-N-X derivative, having all of its amino and hydroxyl functions other than the 5-epi-hydroxyl or 5-hydroxyl function protected, in an inert organic solvent in the temperature range of from about −100° C. to about −50° C., followed by removal of the amino and hydroxyl protecting groups from the so-produced 5-fluoro-5-deoxy or 5-epi-fluoro-5-deoxy-N-protected-O-protected-4,6-di-O-(aminoglycosyl)-1,3-diaminocyclitol, or its 1-N-X derivative.

2. The process of claim 1 including the step of isolating a 5-fluoro-5-deoxy or 5-epi-fluoro-5-deoxy-4,6-di-O-(aminoglycosyl)-1,3-diaminocyclitol or its 1-N-X derivative.

3. The process of claim 1 wherein the dialkylaminosulfur trifluoride is diethylaminosulfur trifluoride, dimethylaminosulfur trifluoride or pyrrolidinosulfur trifluoride.

4. The process of claim 1 wherein said dialkylaminosulfur trifluoride is diethylaminosulfur trifluoride, said temperature range is from about −80° C. to about −60° C., and said inert organic solvent is methylene chloride.

5. The process of claim 1 wherein said 4,6-di-O-(aminoglycosyl)-1,3-diaminocyclitol is a member selected from the group consisting of gentamicin A, gentamicin B, gentamicin $B_1$, gentamicin $C_1$, gentamicin $C_{1a}$, gentamicin $C_2$, gentamicin $C_{2a}$, gentamicin $C_{2b}$, gentamicin $X_2$, sisomicin, verdamicin, tobramycin, Antibiotic G-418, Antibiotic 66-40B, Antibiotic 66-40D, Antibiotic JI-20A, Antibiotic JI-20B, Antibiotic G-52, kanamycin A, kanamycin B, 3′,4′-dideoxykanamycin B and their 5-epi analogs and the 1-N-X derivatives of the foregoing, wherein X is $CH_2Y$.

6. A 5-fluoro-5-deoxy or 5-epi-fluoro-5-deoxy derivative of a 4,6-di-O-(aminoglycosyl)-1,3-diaminocyclitol wherein said 4,6-di-O-(aminoglycosyl)-1,3-diaminocyclitol is selected from the group consisting of gentamicin A, gentamicin B, gentamicin $B_1$, gentamicin $C_{2a}$, gentamicin $C_{2b}$, gentamicin $X_2$, verdamicin, tobramycin, Antibiotic G-418, Antibiotic 66-40B, Antibiotic 66-40D, Antibiotic JI-20A, Antibiotic JI-20B, Antibiotic G-52, kanamycin A, kanamycin B and 3′,4′-dideoxykanamycin B;

and the 1-N-X derivatives thereof, wherein X is —$CH_2Y$ or wherein Y is a member selected from the group consisting of hydrogen, alkyl, alkenyl, cycloalkyl, cycloalkylalkyl, hydroxyalkyl, aminoalkyl, alkylaminoalkyl, aminohydroxyalkyl and alkylaminohydroxyalkyl, said Y having up to 4 carbon atoms and when substituted by both amino and hydroxy groups, said groups are on different carbon atoms; and the pharmaceutically acceptable acid addition salt thereof.

7. A compound of claim 6 which is 5-epi-fluoro-5-deoxyverdamicin.

8. A compound of claim 6 which is 5-fluoro-5-deoxyverdamicin.

9. A compound of claim 6 which is 5-epi-fluoro-5-deoxytobramycin.

10. A compound claim 6 which is 5-fluoro-5-deoxytobramycin.

* * * * *